US012740998B2

(12) United States Patent
Zhong et al.

(10) Patent No.: US 12,740,998 B2
(45) Date of Patent: Sep. 22, 2026

(54) FISH SWIM BLADDER-DERIVED HEPARIN-LIKE MUCOPOLYSACCHARIDE AND METHODS OF MAKING AND USING THE SAME

(71) Applicants: GUANGDONG OCEAN UNIVERSITY, Zhanjiang City (CN); SHENZHEN INSTITUTE OF GUANGDONG OCEAN UNIVERSITY, Shenzhen (CN)

(72) Inventors: Saiyi Zhong, Zhanjiang City (CN); Siyi Zhou, Zhanjiang City (CN); Jing Chen, Zhanjiang City (CN); Jianping Chen, Zhanjiang City (CN); Suhua Chen, Zhanjiang City (CN); Rui Li, Zhanjiang City (CN); Xuejing Jia, Zhanjiang City (CN); Xiaofei Liu, Zhanjiang City (CN)

(73) Assignees: GUANGDONG OCEAN UNIVERSITY, Zhanjiang City (CN); SHENZHEN INSTITUTE OF GUANGDONG OCEAN UNIVERSITY, Shenzhen (CN)

( * ) Notice: Subject to any disclaimer, the term of this patent is extended or adjusted under 35 U.S.C. 154(b) by 759 days.

(21) Appl. No.: 18/020,944

(22) PCT Filed: Nov. 20, 2020

(86) PCT No.: PCT/CN2020/127708
§ 371 (c)(1),
(2) Date: Feb. 13, 2023

(87) PCT Pub. No.: WO2022/062101
PCT Pub. Date: Mar. 31, 2022

(65) Prior Publication Data

US 2023/0293574 A1 Sep. 21, 2023

(30) Foreign Application Priority Data

Sep. 22, 2020 (CN) ........................ 202011001303.7

(51) Int. Cl.

| | |
|---|---|
| ***A61K 31/727*** | (2006.01) |
| ***A61K 35/60*** | (2006.01) |
| ***A61P 9/00*** | (2006.01) |
| ***C08B 37/00*** | (2006.01) |
| ***C12P 19/04*** | (2006.01) |

(52) U.S. Cl.
CPC ............ *A61K 31/727* (2013.01); *A61K 35/60* (2013.01); *A61P 9/00* (2018.01); *C08B 37/0075* (2013.01); *C12P 19/04* (2013.01)

(58) Field of Classification Search
CPC ......... A61K 31/727; A61K 35/60; A61P 9/00; C08B 37/0075; C12P 19/04
USPC .......................................................... 514/56
See application file for complete search history.

(56) References Cited

FOREIGN PATENT DOCUMENTS

| | | | |
|---|---|---|---|
| CN | 106967186 | A | 7/2017 |
| CN | 109251255 | A | 1/2019 |
| JP | 2017081851 | A | 5/2017 |
| WO | 2011122321 | A1 | 10/2011 |

OTHER PUBLICATIONS

Linhardt et al. Analysis of glycosaminoglycan-derived oligosaccharides using fast-atom-bombardment mass-spectrometry. Carbohydrate Research, 225 (1992) 137-145. (Year: 1992).*

Zhou et al. Isolation, purification and structural identification of heparinoids from fish swim bladder[J]. Food Science, 2019, 40(15): 84-91. Published on Aug. 15, 2019 (in Chinese with English abstract) DOI:10.7506/spkx1002-6630-20180728-351. (Year: 2019).*

Zhou et al. Isolation, purification and structural identification of heparinoids from fish swim bladder[J]. Food Science, 2019, 40(15): 84-91. Published on Aug. 15, 2019 (machine English translation). (Year: 2019).*

* cited by examiner

*Primary Examiner* — Yih-Horng Shiao
(74) *Attorney, Agent, or Firm* — Zhigang Ma

(57) ABSTRACT

The present disclosure provides an application of fish swim bladder-derived heparin-like mucopolysaccharide in the preparation of angiogenesis inhibitors, belonging to the technical field of medication. In the present disclosure, the structural unit of the fish swim bladder-derived heparin-like mucopolysaccharide is α-ΔGlcUA-[1→3]-GalNAc-4S. The fish swim bladder-derived heparin-like mucopolysaccharide has strong inhibition on angiogenesis. As shown from the results of examples in the present disclosure, the inhibitory rate of 400 mg/L fish swim bladder-derived heparin-like mucopolysaccharide on the growth of human umbilical vein endothelial cells can be up to 90.3%; and the inhibitory rate of 1 mg/mL fish swim bladder-derived heparin-like mucopolysaccharide on the angiogenesis of chick embryo chorioallantoic membrane is 77.15%.

7 Claims, 8 Drawing Sheets

Note:

ΔDi-0S: $R_2$, $R_4$, $R_6$ are all H;

ΔDi-UA-2S: $R_2$ is $SO_3$-; $R_4$, $R_6$ are both H;

ΔDi-4S: $R_4$ is $SO_3$-; $R_2$, $R_6$ are both H;

ΔDi-6S: $R_6$ is $SO_3$-; $R_2$, $R_4$ are both H.

FISH SWIM BLADDER-DERIVED HEPARIN-LIKE MUCOPOLYSACCHARIDE AND METHODS OF MAKING AND USING THE SAME

This application claims priority to Chinese Patent Application No. 202011001303.7, entitled "APPLICATION OF FISH SWIM BLADDER-DERIVED HEPARIN-LIKE MUCOPOLYSACCHARIDE IN THE PREPARATION OF ANGIOGENESIS INHIBITORS", filed to China National Intellectual Property Administration on Sep. 22, 2020, the entire contents of which are incorporated herein by reference.

TECHNICAL FIELD

The present disclosure pertains to the technical field of medication, and specifically pertains to fish swim bladder-derived heparin-like mucopolysaccharide and methods of making and using the same.

BACKGROUND

Fish swim bladder, also known as fish glue, is a collagenous capsule mainly responsible for ups and downs in the cavity of fish body. Fish swim bladders have a long history of consumption in the coastal areas of China. As a traditional marine aquatic food resource in China which can be used as medicine and food, fish swim bladder is known as "Ginseng in Fish" reputation, which is a traditional Chinese medicine (Compendium of Materia Medica, National Chinese Medicine Assembly). As a traditional Chinese medicine, fish swim bladder has unique nourishing effects and medicinal values, and has the effects of tonifying the kidney and strengthening the essence, nourishing the meridians, stopping excess bleeding, removing blood stasis and reducing swelling. However, there have been no related reports about its utilization in inhibiting angiogenesis.

SUMMARY

In view of this, the objective of the present disclosure is to provide an application of fish swim bladder-derived heparin-like mucopolysaccharide in the preparation of angiogenesis inhibitors, where the fish swim bladder-derived heparin-like mucopolysaccharide has strong inhibition on angiogenesis.

To realize the above objective, the present disclosure provides the following technical solution:

The present disclosure provides an application of fish swim bladder-derived heparin-like mucopolysaccharide in the preparation of angiogenesis inhibitors, where the structural unit of the fish swim bladder-derived heparin-like mucopolysaccharide is α-ΔGlcUA-[1→3]-GalNAc-4S.

Preferably, the fish swim bladder-derived heparin-like mucopolysaccharide is prepared by a process including the following steps:

Fish swim bladder dry powder is mixed with water to get a suspension of fish swim bladder powder;

The suspension of fish swim bladder powder is mixed with sodium chloride and a protease for enzymolysis to get enzymatic hydrolyzate;

The enzymatic hydrolyzate is inactivated and then centrifuged to get a supernatant;

The supernatant is successively adsorbed by macroporous anion-exchange resin and eluted with an aqueous solution of sodium chloride to get an eluate;

The eluate is precipitated and dried to get the fish swim bladder-derived heparin-like mucopolysaccharide.

Preferably, the mass of sodium chloride is 1.2~1.8% of the mass of the fish swim bladder dry powder;

The mass of the protease is 0.5~3.0% of the mass of the fish swim bladder dry powder.

Preferably, the concentration of the aqueous solution of sodium chloride is 0.3~1.1 mol/L.

Preferably, the blood vessels include human umbilical veins or chick embryo chorioallantoic membrane blood vessels.

Preferably, the effective inhibitory concentration of the fish swim bladder-derived heparin-like mucopolysaccharide on the human umbilical veins is 100~500 mg/mL.

Preferably, the effective inhibitory concentration of the fish swim bladder-derived heparin-like mucopolysaccharide on the chick embryo chorioallantoic membrane blood vessels is 0.5~2 mg/mL.

The present disclosure provides an application of fish swim bladder-derived heparin-like mucopolysaccharide in the preparation of angiogenesis inhibitors, where the structural unit of the fish swim bladder-derived heparin-like mucopolysaccharide is α-ΔGlcUA-[1→3]-GalNAc-4S. In the present disclosure, the fish swim bladder-derived heparin-like mucopolysaccharide (HSB for short) has strong inhibition on angiogenesis. As shown from the results of examples in the present disclosure, the inhibitory rate of 400 mg/L fish swim bladder-derived heparin-like mucopolysaccharide on the growth of human umbilical vein endothelial cells can be up to 90.3%; and the inhibitory rate of 1 mg/mL fish swim bladder-derived heparin-like mucopolysaccharide on the angiogenesis of chick embryo chorioallantoic membrane is 77.15%.

DETAILED DESCRIPTION

Figure 1:
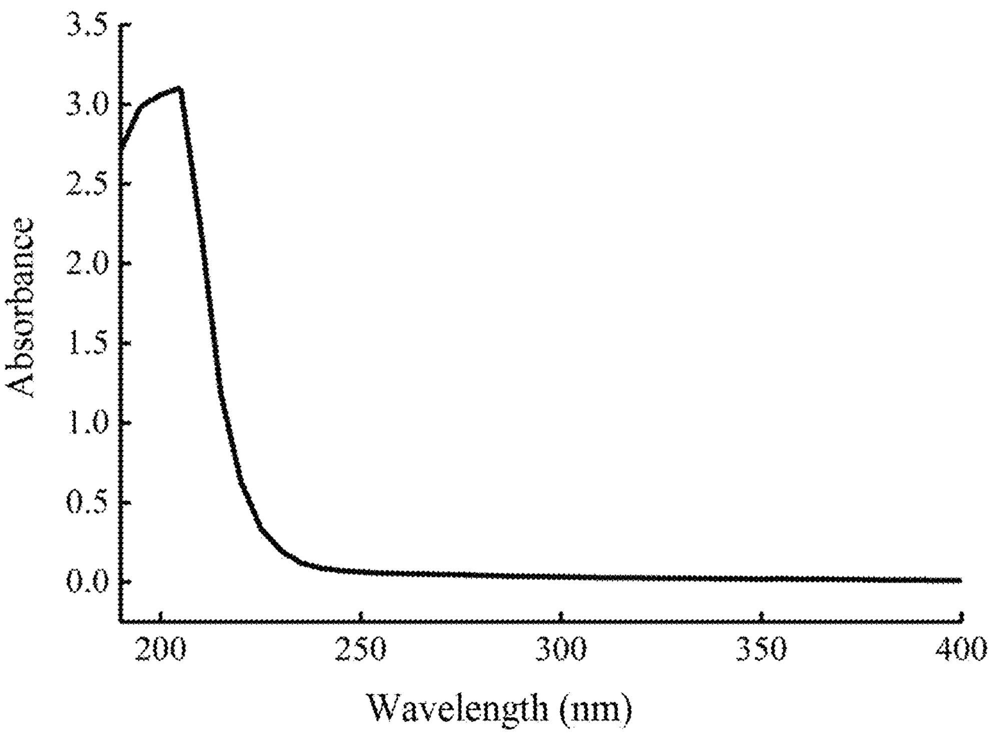
FIG. 1 is the ultraviolet spectrogram of HSB.

The present disclosure provides an application of fish swim bladder-derived heparin-like mucopolysaccharide in the preparation of angiogenesis inhibitors, where the structural unit of the fish swim bladder-derived heparin-like mucopolysaccharide is α-ΔGlcUA-[1→3]-GalNAc-4S.

In the present disclosure, the fish swim bladder-derived heparin-like mucopolysaccharide is prepared by a process preferably including the following steps:

- Fish swim bladder dry powder is mixed with water to get a suspension of fish swim bladder powder;
- The suspension of fish swim bladder powder is mixed with sodium chloride and a protease for enzymolysis to get enzymatic hydrolyzate;
- The enzymatic hydrolyzate is inactivated and then centrifuged to get a supernatant;
- The supernatant is successively adsorbed by macroporous anion-exchange resin and eluted with an aqueous solution of sodium chloride to get an eluate;
- The eluate is precipitated and dried to get the fish swim bladder-derived heparin-like mucopolysaccharide.

The present disclosure mixes fish swim bladder dry powder with water to get a suspension of fish swim bladder powder. In the present disclosure, the particle size of the fish swim bladder dry powder is preferably 150~300 μm, and more preferably 200~250 μm. In the present disclosure, the fish swim bladder dry powder is generated preferably by drying and then crushing the fish swim bladder. In the present disclosure, the drying temperature is preferably 40~60° C., and more preferably 50° C.; There is no special limitation on the drying time in the present disclosure, until a constant weight. There is no special limitation on the crushing ways in the present disclosure, as long as the fish swim bladder dry powder of the particle size as described in the above technical solution can be obtained.

In the present disclosure, the mass ratio of the fish swim bladder dry powder to water is preferably 1:(20~35), and more preferably 1:(25~30).

After obtaining a suspension of fish swim bladder powder, the suspension of fish swim bladder powder is mixed with sodium chloride and a protease for enzymolysis to get enzymatic hydrolyzate.

In the present disclosure, the mass of sodium chloride is preferably 1.2~1.8% of the mass of the fish swim bladder dry powder, more preferably 1.4~1.6%, and most preferably 1.5%. The addition of sodium chloride at the above proportion in the present disclosure can enhance the solubility of protein in the fish swim bladder, improve the efficiency of enzymolysis, and promote the separation of polysaccharides from glycoproteins.

In the present disclosure, the mass of the protease is preferably 0.5~3.0% of the mass of the fish swim bladder dry powder, more preferably 1~2.5%, and most preferably 1.5~2.0%.

There is no special limitation on the varieties of protease, any protease well known to the person skilled in the art can be used. In the examples of the present disclosure, the protease is preferably 2709 alkaline protease.

In the present disclosure, the enzymolysis temperature is preferably 45~60° C., more preferably 45~55° C., and most preferably 50° C.; the enzymolysis time is preferably 18~20 h, and more preferably 19 h; and the pH value is preferably 7.5~9, and more preferably 8~8.5. There is no special limitation on the reagent used to adjust the pH value in the present disclosure, and any bases well known to the person skilled in the art can be used, particularly such as sodium hydroxide or potassium hydroxide. In the present disclosure, during enzymolysis, proteins in the fish swim bladder are enzymatically hydrolyzed to release heparinoid.

After obtaining the enzymatic hydrolyzate, it is inactivated and then centrifuged to get a supernatant. In the present disclosure, the enzyme inactivation is preferably high-temperature inactivation; and the temperature for the high-temperature inactivation is preferably 90~110° C., and more preferably 100° C. In examples of the present disclosure, the temperature for the enzyme inactivation is preferably provided by a boiling water bath; and the time for the enzyme inactivation is preferably 8~12 min, and more preferably 10 min.

After enzyme inactivation, the present disclosure preferably further includes cooling the enzyme inactivation system to room temperature. There is no special limitation on the cooling ways in the present disclosure, and any cooling ways well known to the person skilled in the art can be used.

In the present disclosure, the temperature for centrifugation is preferably room temperature; the centrifugal speed is preferably 7000~9000 r/min, and more preferably 8000 r/min; and the time for centrifugation is preferably 15~25 min, and more preferably 20 min.

After obtaining the supernatant, it is successively adsorbed by macroporous anion-exchange resin and eluted with an aqueous solution of sodium chloride, and the resulting eluate is precipitated and dried to get the fish swim bladder-derived heparin-like mucopolysaccharide.

In the present disclosure, the pore diameter of the macroporous anion-exchange resin is preferably 600~800 μm, more preferably 650~750 μm, and most preferably 700 μm. The macroporous anion-exchange resin preferably includes FPA98Cl, D218, D204, D208, D254, D301 macroporous anion-exchange resins.

In the present disclosure, the macroporous anion-exchange resin has a high reuse rate. The used macroporous anion-exchange resin can be treated by a process including the following steps: the used macroporous anion-exchange resin is successively immersed in water, treated with a regenerated solution and washed with water. In the present disclosure, the temperature for water immersion is preferably room temperature; and the time is preferably 10~14 h, and more preferably 12 h. During the water immersion, the macroporous anion-exchange resin swells fully. In the present disclosure, the regenerated solution preferably comprises the following components: 8~12 wt % of sodium chloride, 0.3~0.5 wt % of sodium hydroxide and the remaining water. The content of sodium chloride is preferably 10 wt %, and the content of sodium hydroxide is preferably 0.4 wt %. The volume ratio of the swollen macroporous anion-exchange resin to the regenerated solution is preferably 1:(3~5), and more preferably 1:4. In the present disclosure, the time for regenerated solution treatment is preferably 1~3 h, and more preferably 2 h. Ions and other impurities adsorbed in the used macroporous anion-exchange resin can be removed during treatment by the regenerated solution, thereby restoring its original composition and properties. In the present disclosure, the washing is preferably performed with distilled water. There is no special limitation on the times of washing in the present disclosure, until the effluent is neutral. Washing aims to remove the regenerated solution.

In the present disclosure, the adsorption mode is preferably dynamic adsorption. The adsorption temperature is preferably 40~50° C., and more preferably 45° C. In the present disclosure, the flow rate at which the supernatant flows through the macroporous anion-exchange resin chromatographic column is preferably 0.5~2 times of column bed volume/h, and more preferably 1~1.5 times of column bed volume/h. There is no special limitation on the specification of the chromatographic column in the present disclosure, and chromatographic columns of any specification well known to the person skilled in the art can be used. In examples of the present disclosure, the specification of the chromatographic column is preferably 0.28 cm×100 cm. In the present disclosure, the loading quantity of the supernatant is preferably 3~8 times of column bed volume, and more preferably 4~6 times of column bed volume. In the present disclosure, during the adsorption, the supernatant is dynamically adsorbed on the macroporous anion-exchange resin selectively to separate out part of impure proteins and nucleic acids.

After the adsorption, the present disclosure preferably further includes washing the pretreated macroporous anion-exchange resin chromatographic column with water. There is no special limitation on the washing times in the present disclosure, until the effluent is colorless and transparent.

In the present disclosure, the concentration of the aqueous solution of sodium chloride is preferably 0.1~1.5 mol/L. In the present disclosure, the elution is preferably gradient elution. In particular, the gradient elution is conducted with aqueous solutions of sodium chloride at concentrations of 0.3 mol/L, 0.5 mol/L, 0.9 mol/L and 1.1 mol/L successively. In the present disclosure, an eluate of sodium chloride at 1.1 mol/L is collected during the gradient elution, and the content of heparinoid in the tube is traced by an Alcian blue assay.

After obtaining the eluate, it is precipitated and dried to get the fish swim bladder-derived heparin-like mucopolysaccharide. In the present disclosure, the reagent used for precipitation is preferably absolute ethanol, and the volume ratio of absolute ethanol to the eluate is preferably (0.8~1.5): 1, and more preferably 1:1; and the precipitation time is preferably 10~14 h, and more preferably 12 h.

In the present disclosure, after the precipitation, the present disclosure preferably further includes centrifuging the precipitated system, washing the resulting solid product with absolute ethanol and desalting with a dialysis bag. In the present disclosure, the centrifugal speed is preferably 3500~4500 r/min, and more preferably 4000 r/min; and the time for centrifugation is preferably 4~6 min, and more preferably 5 min. In the present disclosure, the times of absolute ethanol washing is preferably 2~3 times. In the present disclosure, the molecular weight cut-off of the dialysis bag is preferably 1000~3000 Da, and more preferably 2000 Da. There is no special limitation on the desalination operations of the dialysis bag in the present disclosure, as long as sodium chloride in the system can be removed.

In the present disclosure, the drying mode is preferably freeze-drying, and the freeze-drying is preferably conducted in a freezing dryer. There are no special limitations on the freeze-drying temperature and time in the present disclosure, until a constant weight.

In the present disclosure, the blood vessels preferably include human umbilical veins or chick embryo chorioallantoic membrane blood vessels. In the present disclosure, the effective inhibitory concentration of the fish swim bladder-derived heparin-like mucopolysaccharide on chick embryo chorioallantoic membrane blood vessels is preferably 0.5~2 mg/mL, and more preferably 1~1.5 mg/mL. In the present disclosure, the effective inhibitory concentration of the fish swim bladder-derived heparin-like mucopolysaccharide on human umbilical veins is preferably 100~500 mg/mL, and more preferably 300~400 mg/mL.

The present disclosure will be further illustrated below in combination with examples and accompanying drawings.

Example 1

The fish swim bladder was dried in an oven at 50° C. to a constant weight, and crushed to get fish swim bladder dry powder with a particle size of 150~300 μm; the fish swim bladder dry powder was mixed with distilled water at a mass ratio of 1:20 to get a suspension of fish swim bladder powder.

400 mL of the suspension of fish swim bladder powder was mixed with 6 g sodium chloride and 8 g 2709 alkaline protease and enzymatically digested at 50° C. for 20 h to get enzymatic hydrolyzate.

The enzymatic hydrolyzate is inactivated in a boiling water bath for 10 min, cooled to room temperature and then centrifuged at 8000 r/min for 20 min to get a supernatant.

Rohm and Hass FPA98 Cl resin was immersed in distilled water for 12 h, treated by adding a regenerated solution for 2 h, and washed with distilled water to neutral; the resulting pretreated FPA98 Cl resin was placed in a chromatographic column (0.28 cm×100 cm) to get the chromatographic column with pretreated FPA98 Cl resin; wherein, the regenerated solution was composed of 10 wt % sodium chloride, 0.4 wt % sodium hydroxide and the remaining water; and the volume ratio of the regenerated solution to Rohm and Hass FPA98 Cl resin was 5:1.

The supernatant was injected into the chromatographic column with pretreated FPA98 Cl resin at a flow rate of 1.5 times of column bed volume/h, and adsorbed dynamically at 45° C. The chromatographic column was rinsed with distilled water until the effluent was colorless and transparent, then eluted with aqueous solutions of sodium chloride at gradient concentrations of 0.3 mol/L, 0.5 mol/L, 0.9 mol/L and 1.1 mol/L successively. The eluates resulted from the elution with aqueous solutions of sodium chloride at 0.3 mol/L, 0.5 mol/L, 0.9 mol/L and 1.1 mol/L respectively were collected and marked as eluate F1, eluate F2, eluate F3 and eluate F4 successively;

Absolute ethanol was added into the eluates F1~F4 respectively for precipitation. After standing for 12 h, they were centrifuged at 4000 r/min for 5 min. The resulting solid products were washed with absolute ethanol for 2 times, desalinated through a dialysis bag of 3000 kDa, and freeze-dried in a freezing dryer to a constant weight, thus successively obtaining an elution component F1, an elution component F2, an elution component F3 and fish swim bladder-derived heparin-like mucopolysaccharide F4 (the fish swim bladder-derived heparin-like mucopolysaccharide F4 was marked as HSB for short).

(1) Determination on the Basic Components of the Fish Swim Bladder-Derived Heparin-Like Mucopolysaccharide The content of the fish swim bladder-derived heparin-like mucopolysaccharide was determined by an Alcian blue assay with heparin as the standard;

The content of protein was determined by a Folin-phenol reagent method with bovine serum albumin as the standard;

The content of uronic acid was determined by a carbazole-sulphuric acid method with glucuronic acid as the standard;

The content of hexosamine was determined by a Wagner method with glucosamine as the standard;

The content of sulfate group was determined by a $BaCl_2$-gel turbidimetric method with potassium sulfate as the standard.

The yield of the fish swim bladder-derived heparin-like mucopolysaccharide from the eluates F1~F4 was calculated following the formula (1), and the content of test index of each component in the fish swim bladder-derived heparin-like mucopolysaccharide was calculated following the formula (2), and the basic components of the fish swim bladder-derived heparin-like mucopolysaccharide were as shown in Table 1.

$$\text{Yield}/(\text{mg/g}) = \frac{m_{d1}}{m_{d2}} \times 1000; \quad \text{Formula (1)}$$

In formula (1): $m_{d1}$ represents the mass of the fish swim bladder-derived heparin-like mucopolysaccharide, in a unit of g; $m_{d2}$ represents the mass of the fish swim bladder dry powder, in a unit of g.

$$\text{Content}/\% = \frac{c \times V}{m_{d1}} \times 100\%; \quad \text{Formula (2)}$$

In formula (2), c represents the content of test index of each component, in a unit of mg/mL; $m_{d1}$ represents the mass of the fish swim bladder-derived heparin-like mucopolysaccharide, in a unit of mg; and V represents the volume of the eluate, in a unit of mL.

TABLE 1

The yield of the fish swim bladder-derived heparin-like mucopolysaccharide from each eluate and the contents of various components in the fish swim bladder-derived heparin-like mucopolysaccharide

| Eluate | Yield/(mg/g) | Heparinoid/% | Protein/% | Uronic acid/% | Hexosamine/% | Sulfate group /% |
|---|---|---|---|---|---|---|
| F1 | 0.07 ± 0.01 | 0.66 ± 0.02 | 46.26 ± 0.78 | ND | ND | ND |
| F2 | 0.79 ± 0.03 | 53.01 ± 1.25 | 19.97 ± 0.47 | 22.32 ± 0.50 | 18.16 ± 1.87 | ND |
| F3 | 0.14 ± 0.02 | 62.02 ± 1.03 | 19.04 ± 0.83 | 25.50 ± 0.70 | 26.87 ± 1.49 | 9.32 ± 1.68 |
| F4 | 2.21 ± 0.03 | 85.79 ± 0.63 | 0.19 ± 0.07 | 29.38 ± 0.18 | 34.33 ± 0.75 | 12.29 ± 2.20 |

In the table, ND indicates not detected.

As can be seen from Table 1, from the eluate F1 to the eluate F4, the contents of heparinoid, uronic acid and hexosamine rise gradually and the content of protein decreases gradually, suggesting that heparinoid can be well separated out by the above process. The yield of heparinoid is the highest in the eluate F4, that is (2.21±0.03) mg/g, followed by F2; while in F1, the content of protein is the highest, the yield and content of heparinoid are both low, and the contents of uronic acid and hexosamine cannot be detected, suggesting that F1 may be a mixture of neutral saccharide and protein. The content of sulfate groups is the highest in F4, that is (12.29±2.20)%, followed by F3, and no sulfate groups are detected in the remaining two eluates. The content of sulfate groups is an important index indicating the activity of heparinoid. Within a certain range, the higher the content of sulfate groups, the stronger the biological activity.

(2) Ultraviolet Spectrum Analysis of HSB

HSB was formulated into an HSB solution of 1 mg/ml with distilled water. Using distilled water as the zero-calibration tube, an Agilent Cary 60 ultraviolet and visible spectrophotometer was employed to determine the ultraviolet absorption spectrum of the HSB solution, with the results as shown in FIG. 1.

It was known from FIG. 1 that, except for the absorption of glycosyl terminal at 204 nm, there were no obvious absorption peaks in other ultraviolet regions for the fish swim bladder-derived heparin-like mucopolysaccharide as prepared in Example 1. Combined with the protein content of only (0.19±0.07)% in Table 1, it was indicated that the fish swim bladder-derived heparin-like mucopolysaccharide prepared in the present disclosure has a high degree of purity, with low contents of nucleic acid, protein and other impurities.

(3) High Performance Gel Permeation Chromatography Analysis of HSB

High performance gel permeation chromatography (HPGPC) was employed to determine the purity and molecular weight of HSB. Test conditions: the chromatographic column is Waters Ultrahydrogel Column 500 (7.8 mm×300 mm); the column temperature is 35° C.; the mobile phase is 0.2 mol/L of sodium sulfate, and the flow rate is 0.6 mL/min; the detector is agilent 1200 differential detector; and the sample volume is 10 μL.

Figure 2:
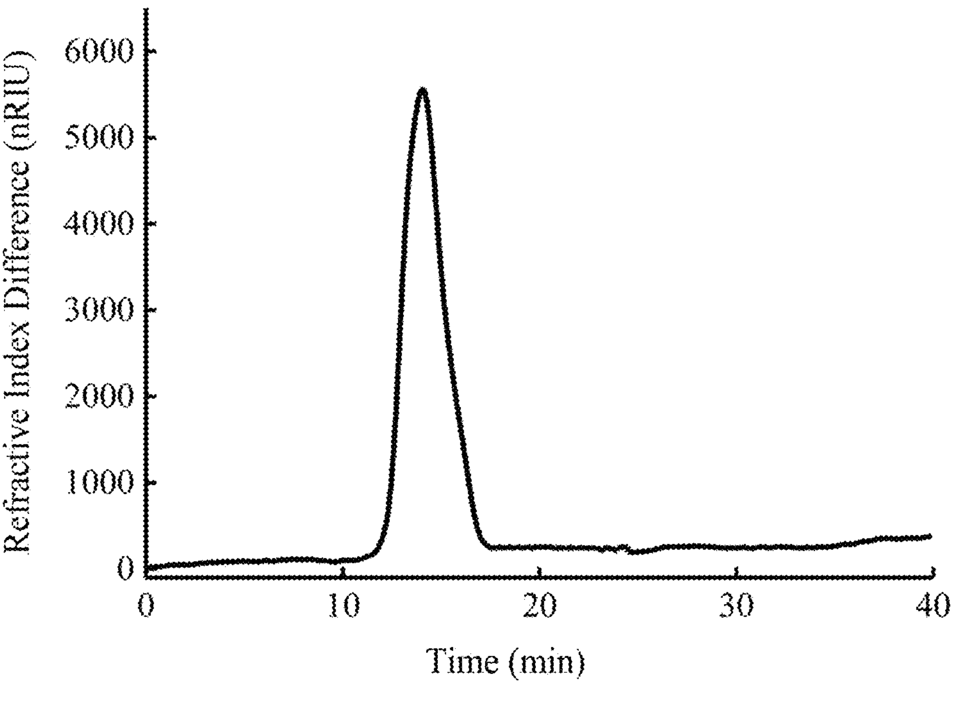
FIG. 2 is the high performance gel chromatogram of HSB.

Glucan standards (10000 u, 25000 u, 50000 u, 80000 u, 150000 u, 270000 u, 410000 u) and HSB were respectively formulated into solutions of 5 mg/mL with 0.2 mol/L of sodium sulfate, which were filtered over a needle filtration membrane of 0.22 μm and then injected. The retention times of Glucan standards and HSB sample were recorded and subjected to data treatment, with the test results shown in FIG. 2. As can be seen from FIG. 2, there was only one peak in the high performance gel chromatogram of HSB and the peak shape was symmetric, suggesting that the mass distribution of HSB was relatively uniform, and the purity was high. By using high performance gel permeation chromatography combined with a differential refraction detector, we can determine the molecular weight of glucan, and the logarithm (y) of the molecular weight and the retention time (x) conform to the following regression equation: y=−0.3192+9.429 ($R^2$=0.9966), from which the molecular mass of HSB was calculated to be 84033 u. The molecular mass of heparinoid is generally in a range of 5000~40000 u. By contrast, the fish swim bladder-derived heparin-like mucopolysaccharide prepared in the present disclosure has large molecular mass.

Figure 3:
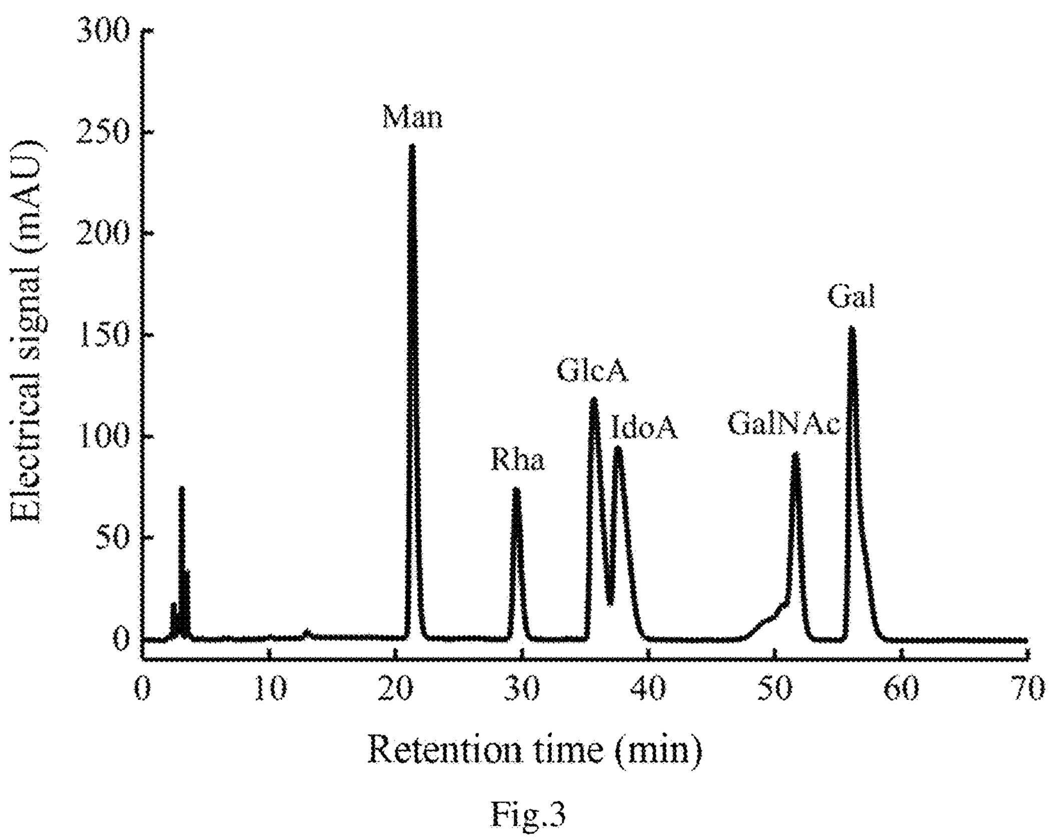
FIG. 3 is the high performance liquid chromatogram of mixed monosaccharide standard.
Figure 4:
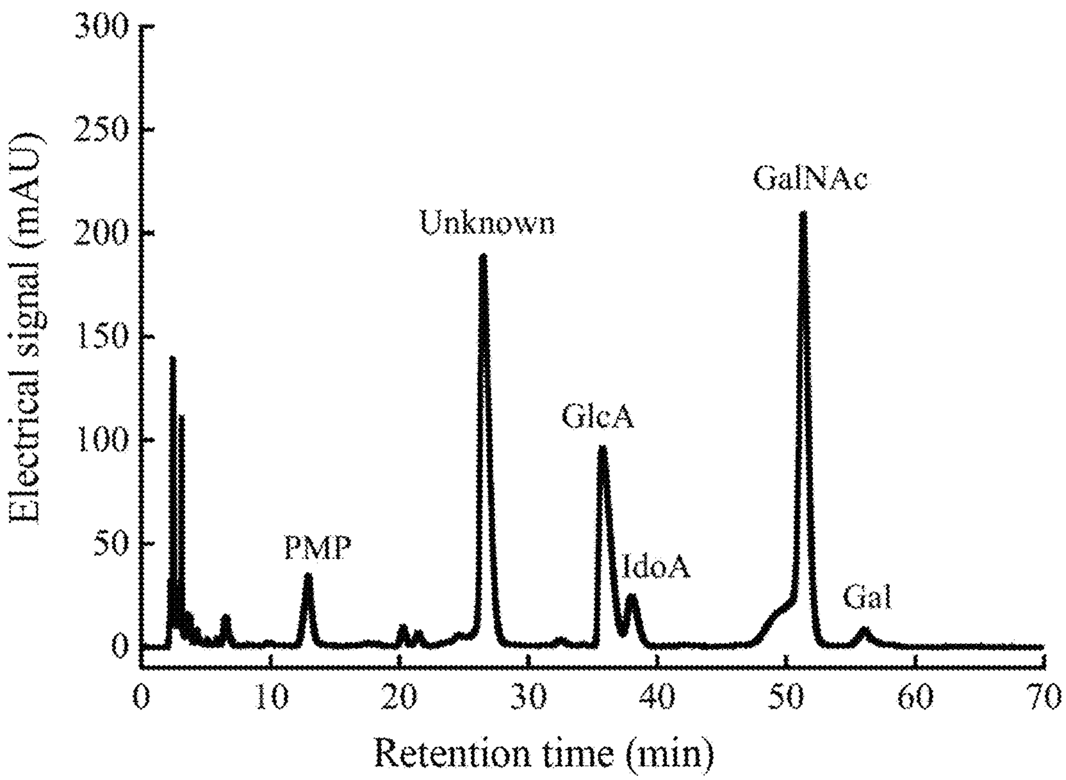
FIG. 4 is the high performance liquid chromatogram of monosaccharide derivatives in HSB.
Figure 5:
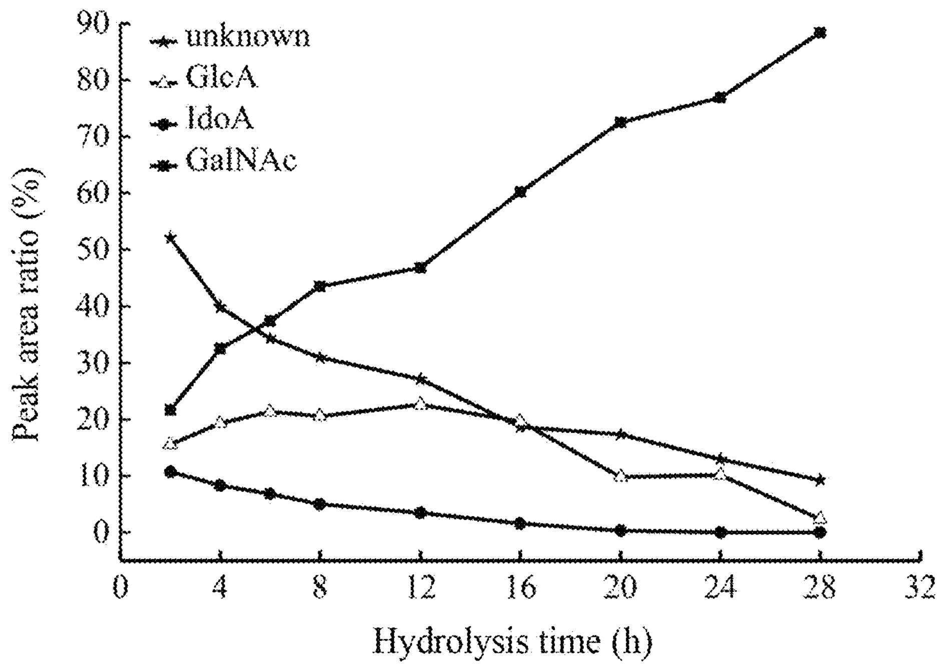
FIG. 5 is a diagram showing the effects of hydrolysis time on the peak area ratio of various components in the hydrolyzed samples of HSB.

(4) Analysis on the Monosaccharide Composition in HSB 3.0 mg HSB was weighed into a 15 mL ampoule, into which was added 9 mL trifluoroacetic acid at 1.5 mol/L, and hydrolyzed in an oven at 110° C. for 2, 4, 6, 8, 12, 16, 24 and 28 h respectively. The resulting hydrolysates were dried by blowing with nitrogen. The blow-dried products were dissolved in ultrapure water to get HSB hydrolyzed samples at different hydrolysis time;

By using monosaccharide standards, the PMP derivation-reversed-phase high performance liquid chromatography (see: WANG Q, ZHAO X, PU J, et al. Influences of acidic reaction and hydrolytic conditions on monosaccharide composition analysis of acidic, neutral and basic polysaccharides [J]. Carbohydrate polymers, 2016, 143: 296-300) was employed to test the contents of various components in the mixed monosaccharide standards, HSB and HSB hydrolyzed samples, with the test results as shown in FIGS. 3-5. Wherein, FIG. 3 is the high performance liquid chromatogram of the mixed monosaccharide standards, FIG. 4 is the high performance liquid chromatogram of the monosaccharide derivative in HSB, and FIG. 5 shows the effects of hydrolysis time on the peak area ratio of each component in HSB hydrolyzed samples. Monosaccharide standards are mannose (Man), rhamnose (Rha), glucuronic acid (GlcA), iduronic acid (IdoA), N-acetylgalactosamine (GalNAc), and galactose (Gal). Test conditions of PMP derivation-reversed-phase high performance liquid chromatography: the chromatographic column is Agilent ZORBAX EclipseXDB-C18 (4.6×250 mm, 5 μm); the column temperature is 30° C.; the mobile phase is 0.02 mol/L of phosphate buffer (pH=6.0)-acetonitrile (volume ratio=83:17), and the flow rate is 1.0 mL/min; the wavelength of the detector is 245 nm; and the sample volume is 10 μL.

As can be seen from FIGS. 3~5, compared with the chromatogram of mixed monosaccharide standards (FIG. 3), it was found that an unknown peak with a very high peak value appeared in the high performance liquid chromatogram of HSB (FIG. 4). It was seen from FIG. 5 that, with the extension of the hydrolysis time of HSB, the peak area ratio of the unknown peak decreased, the peak area ratio of glucuronic acid and iduronic acid also decreased gradually, while the peak area ratio of N-acetyl galactosamine increased continuously, suggesting that the unknown peak represented undegraded oligosaccharide fragments. Due to that uronic acid is unstable in acid solution and prone to decarboxylation, and even may be completely decomposed by strong acids, so the longer the degradation time, the peak area of uronic acid would decrease. According to the peak appearance time and the peak area, it can be known that HSB mainly comprises glucuronic acid, N-acetyl galactosamine and a small amount of iduronic acid and galactose, thereby indicating that the backbone of HSB may be chondroitin sulfate.

Figure 6:
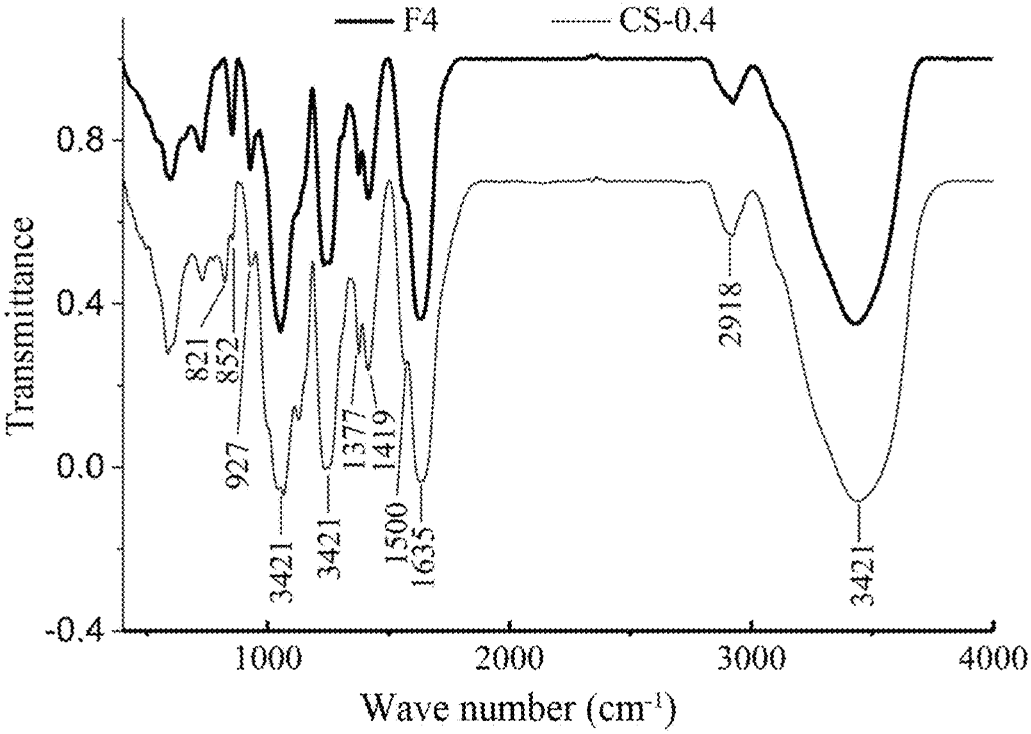
FIG. 6 is the Fourier infrared spectrum of HSB.

(5) Fourier Transform Infrared Spectroscopy of HSB 3 mg HSB was baked under an infrared lamp for 2 h, then put into an agate mortar and mixed uniformly with 300 mg potassium chloride that had been treated in the same manner as HSB. They were ground to granules less than 2.5 μm, and pressed into small translucent sheets in a tablet machine. The small translucent sheets were scanned in a Fourier infrared spectrum scanner within a scan range of 4000~400 $cm^{-1}$, with the results shown in FIG. 6. Wherein, CS-0.4 indicates the transmittance of CS minus 0.4, which is used to distinguish the two curves. It can be seen from FIG. 6 that, the infrared spectrogram of HSB is substantially consistent with that of chondroitin sulfate standard, and the strong and wide peak occurred at 3421 $cm^{-1}$ shows the stretching vibration of O—H and N—H, suggesting that there are intermolecular and intramolecular hydrogen bonds in HSB; the absorption peak at 2918 $cm^{-1}$ indicates the presence of methylene; the strong and slightly wider peak at 1635 $cm^{-1}$ is generated from the symmetrical stretching vibration of C═O in acetamido; there are N—H scissoring vibration at 1500 $cm^{-1}$ and C—N stretching vibration at 1419 $cm^{-1}$, indicating the presence of acetamido; the peak at 1377 $cm^{-1}$ is generated from the symmetrical stretching vibration of C═O in —$COO^-$; the stretching vibration of C═O in the sulfate ester group at 1255 $cm^{-1}$, the stretching vibration of the sulfate group S═O at 1234 $cm^{-1}$ and the axial stretching vibration of C—O—S in the sulfate ester group at 852 $cm^{-1}$ indicate the presence of the sulfate ester group; and the absorption peak at 927 $cm^{-1}$ is generated from the asymmetrical stretching vibration of pyranose ring.

According to the number of sulfate groups in chondroitin sulfate units and the different locations of linkage, chondroitin sulfate is divided into types A, C, D, and E, wherein the sulfate group of chondroitin sulfate A (CSA) is located at C4, generating an axial stretching vibration peak near 850 $cm^{-1}$; the sulfate group of chondroitin sulfate C (CSC) is located at C6, that is, the sulfate group is in the flat position, the absorption peak of which is near 850 $cm^{-1}$; chondroitin sulfate E is the standard, having absorption peaks near both 820 $cm^{-1}$ and 850 $cm^{-1}$; there is only an absorption peak near 850 $cm^{-1}$ for HSB, indicating that HSB may be chondroitin sulfate A or its derivative.

(6) Mass Spectrometry of HSB

To further analyze the chondroitin sulfate composition of HSB, chondroitin sulfate was completely decomposed into unsaturated disaccharides using chondroitinase ABC, and then identified by MS/MS analysis.

0.0100 g HSB was precisely weighed into 5 mL ammonium acetate buffer (pH=7.6~8.0, containing 0.2 U chondroitinase ABC), incubated at 37° C. for 24 h, inactivated in a boiling water bath for 5 min, and centrifuged at 10000 r/min for 25 min. The resulting supernatant was filtered over a 3 kDa ultra-filtration centrifugal tube. The filtrate was freeze-dried to get the treated HSB sample. The treated HSB sample and the chondroitin sulfate standard were respectively formulated into a solution of 1 μg/mL with ultrapure water for mass spectrometry/mass spectrometry analysis.

Conditions for mass spectrometry: Using an electron impact ion source; the electron energy is 70 eV; the temperature of the transmission line is 275° C.; the temperature of ion source is 200° C.; the parent ion is m/z 285; the activation voltage is 1.5 V; and the mass scan range is m/z 35~500.

According to the number of sulfate groups and the linkage locations, chondroitin sulfate is divided into ΔDi-0S, ΔDi-UA-2S, ΔDi-4S and ΔDi-6S. Wherein, ΔDi-4S is the primary chondroitin sulfate unit of CSA, and ΔDi-6S is the primary chondroitin sulfate unit of CSC. In addition, chondroitin sulfates with the same number of sulfate groups have the same relative molecular mass and cannot be distinguished by means of quasi-ion peak regions, so they are distinguished by fragment ions in the secondary mass spectrometry. The MS/MS results of four common chondroitin sulfate standards and the completely degradation products of HSB are shown in Table 2 and FIG. 7, and the basic composition of chondroitin sulfate fragments in HSB is shown in FIG. 8.

TABLE 2

Basic composition of chondroitin sulfate fragments in HSB

| Chondroitin sulfate | Relative molecular weight | MS/MS characteristic fragment peak (m/z) | Fragment structure |
|---|---|---|---|
| ΔDi-0S sodium salt | 401.34 | 202.09 | $[Z_1 - 2H]^-$ |
| ΔDi-UA-2S sodium salt | 503.34 | 202.09 | $[Z_1 - 2H]^-$ |
| | | 236.99 | $[Y_2 - H]^-$ |
| | | 276.98 | $[Z_2 + Na - H]^-$ |

TABLE 2-continued

| Basic composition of chondroitin sulfate fragments in HSB | | | |
|---|---|---|---|
| Chondroitin sulfate | Relative molecular weight | MS/MS characteristic fragment peak (m/z) | Fragment structure |
| ΔDi-4S sodium salt | 503.34 | 282.05 | $[Z_1-2H]^-$ |
| | | 300.06 | $[Y_1-H]^-$ |
| ΔDi-6S sodium salt | 503.34 | 239.94 | $[W_1-H]^-$ |
| | | 282.05 | $[Z_1-2H]^-$ |

Figure 7:
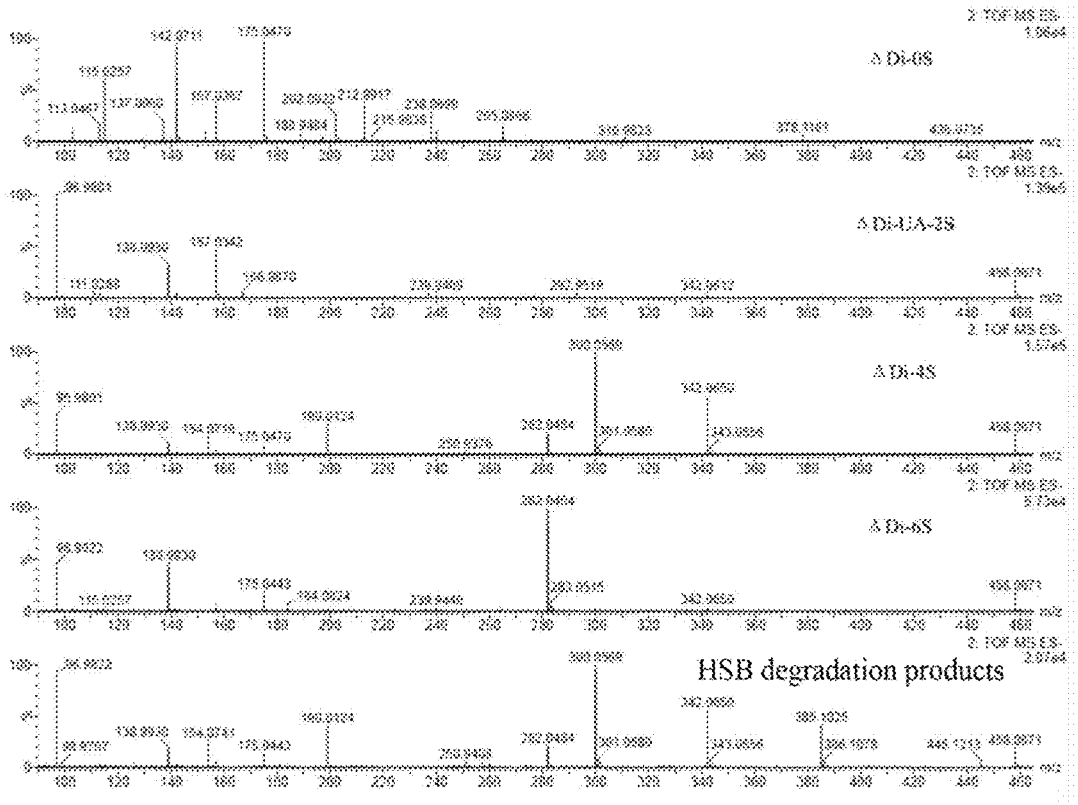
FIG. 7 is the MS/MS spectrums of chondroitin sulfate standards of types A, C, D and E and completely degradation products of HSB.
Figure 8:
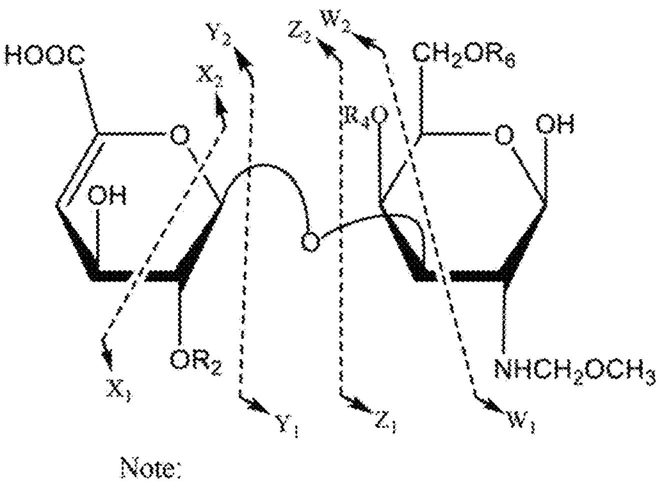
FIG. 8 is a diagram showing the basic composition of chondroitin sulfate fragments in HSB.

It is known from Table 2 and FIGS. 7~8 that, galactosamine of ΔDi-0S and ΔDi-UA-2S does not contain sulfate groups, the structure of its characteristic fragment is $[Z_1\text{-}2H]^-$, and m/z is 202.09; the sulfate group of ΔDi-UA-2S is ligated at the hydroxyl of glucuronic acid $C_2$, thus ΔDi-UA-2S has characteristic fragment structures of $[Y_2\text{—}H]^-$ and $[Z_2\text{+Na—}H]^-$, and its m/z are 236.99 and 276.98, respectively. ΔDi-4S is different from ΔDi-6S in that, the ion abundance of ΔDi-4S at m/z 282 is less than that at m/z 300 or is absent, while the ion abundance of ΔDi-6S at m/z 300 is less than that at m/z 282 or is absent. In FIG. 7, the ion abundance of ΔDi-4S at m/z 300.06 is greater than that at m/z 282.05, the ion abundance of ΔDi-6S at m/z 282.05 is larger and there is no fragment peak at m/z 300.06; and the characteristic peak of ΔDi-6S at m/z 239.94 has a structure of $[W_1\text{—}H]^-$, which can be used to determine the presence of ΔDi-6S. In the mass spectrogram of completely degradation products of HSB: there are no m/z 202.09, 236.99 and 276.98, suggesting that HSB does not contain ΔDi-0S and ΔDi-UA-2S; the ion abundance at m/z 300.06 is greater than that at m/z 282.05, and there is not a characteristic peak of ΔDi-6S at m/z 239.94, suggesting that the primary chondroitin sulfate unit of HSB is ΔDi-4S. It is determined in combination with the scanning results of infrared spectroscopy that HSB is mainly CSA.

(7) Nuclear Magnetic Resonance Analysis of HSB

Figure 9:
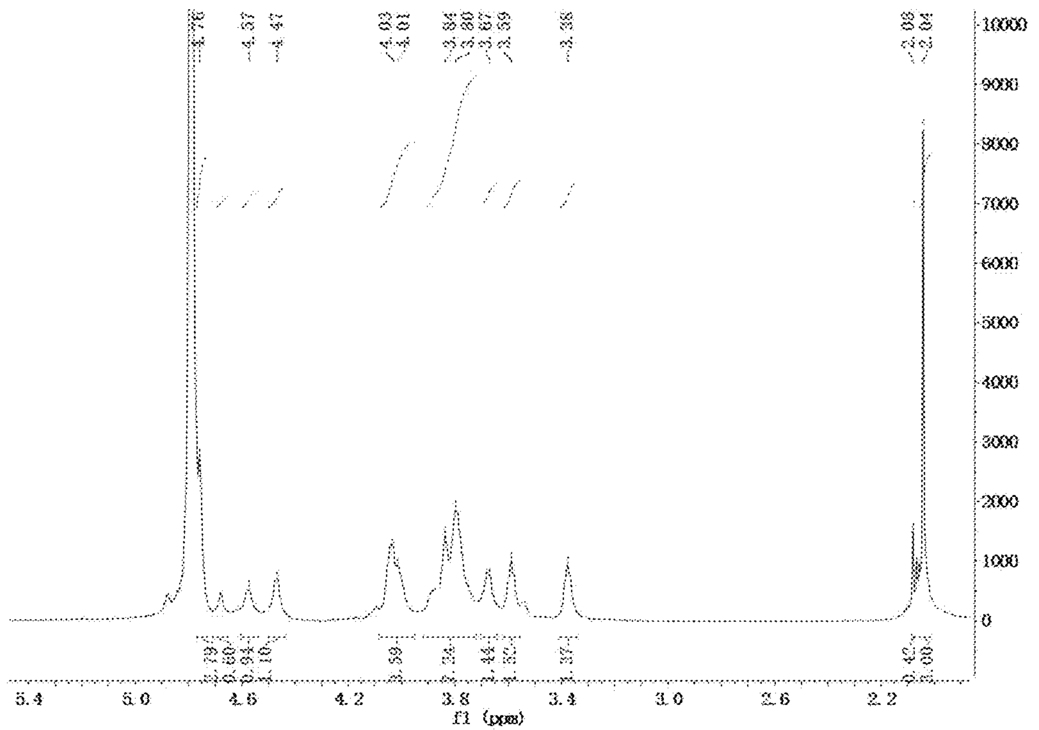
FIG. 9 is the $^{1}$H spectrum of HSB.
Figure 10:
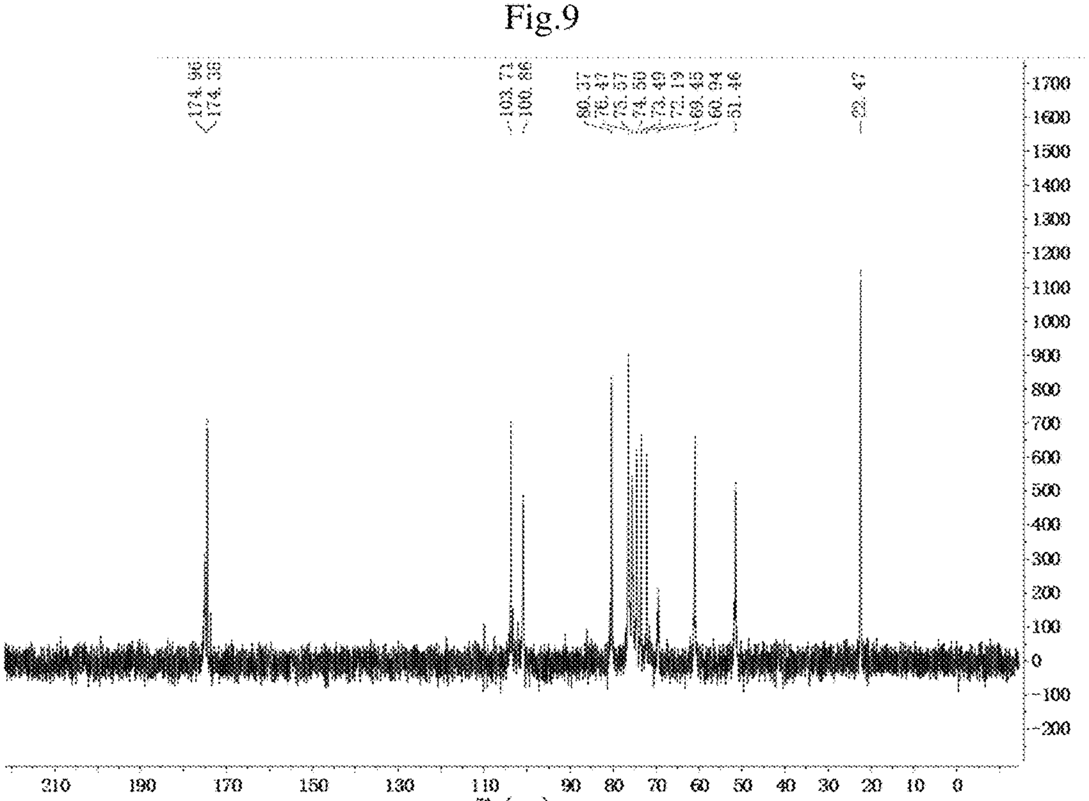
FIG. 10 is the $^{13}$C spectrum of HSB.
Figure 11:
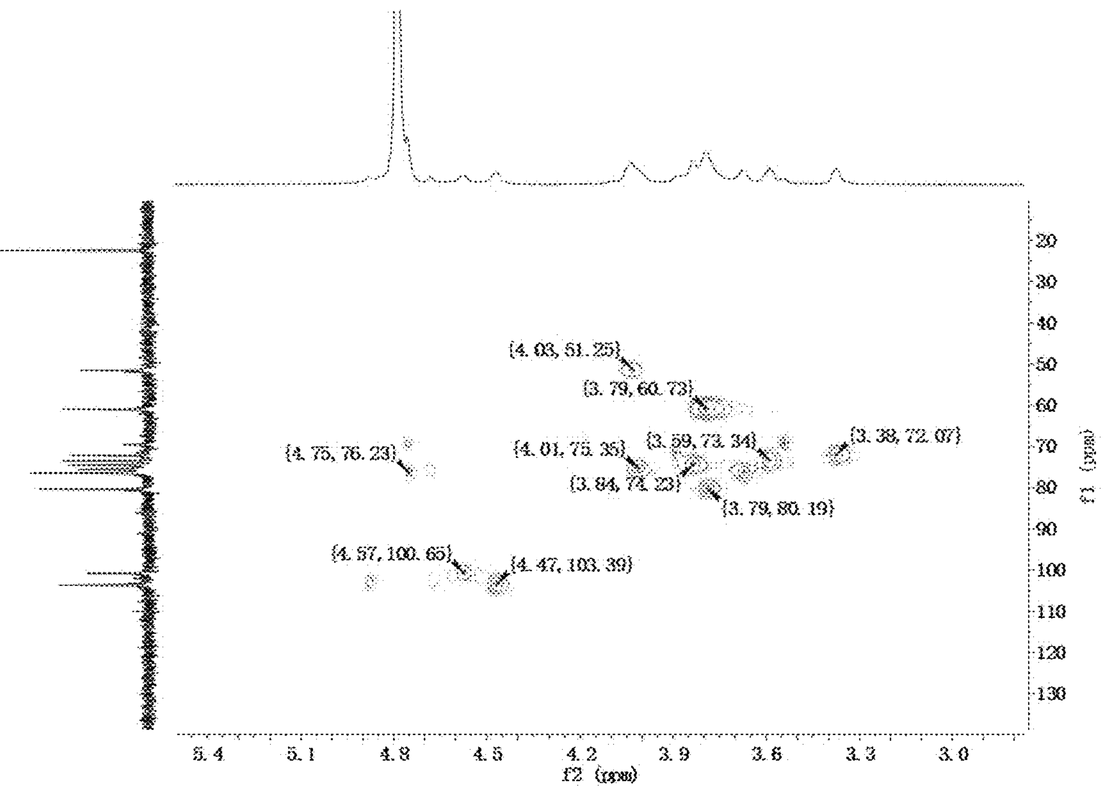
FIG. 11 is the HSQC spectrum of HSB.
Figure 12:
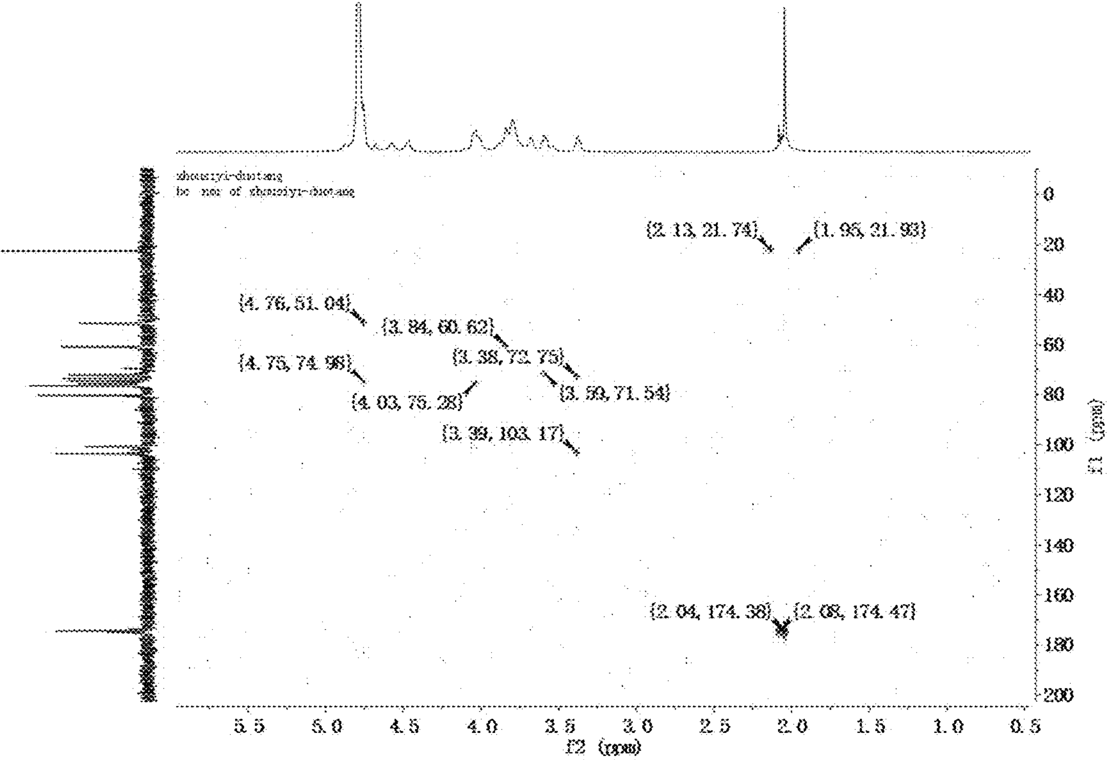
FIG. 12 is the HMBC spectrum of HSB.

HSB was dissolved in $D_2O$ and then freeze-dried, repeatedly for three times to displace out $H_2O$. The treated sample was formulated with $D_2O$ into a solution of 30 mg/mL, which was analyzed at normal temperature in a 700M nuclear magnetic resonance spectrometer for $^1H$ spectrum, $^{13}C$ spectrum, heteronuclear single quantum coherence spectrum (HSQC) and heteronuclear multiple bond correlation (HMBC), with the results shown in FIGS. 9~12. Wherein, FIG. 9 shows $^1H$ spectrum, FIG. 10 shows $^{13}C$ spectrum, FIG. 11 shows HSQC spectrum, and FIG. 12 shows HMBC spectrum.

As known from FIGS. 9~12, in the $^1H$ spectrum, the peak where the proton signal is strongest is located at 4.79 ppm, which is the solvent peak generated from deuterated water. Besides this, all the proton signals are located in the two spectral regions. The acetamide methyl signals appear between 2.0~2.1 ppm, wherein the acetamide methyl signals of CSA and CSC appear at 2.04 ppm and 2.02 ppm respectively; and the acetamide methyl signal of HSB is located at 2.04 ppm, suggesting that HSB may be CSA; other proton signals are concentrated between 3~5 ppm, suggesting that HSB is in an β-configuration. In the $^{13}C$ spectrum, the low-field signals at 174.96 ppm and 174.35 ppm indicate the presence of acetamido and carboxyl of hexuronic acid; and the high-field signal at 22.45 ppm may be acetamide methyl carbon; other signals are concentrated between 50-105 ppm. In addition, it is determined from HSQC spectrum (2.04 ppm, 22.45 ppm) and HMBC spectrum (2.04 ppm, 174.38 ppm) that 22.45 ppm shows the methyl carbon signal of acetamido, 2.04 ppm shows the methyl proton signal of acetamido, and 174.38 ppm shows the carbonyl carbon signal of acetamido. With reference to the document (TOIDA T, TOYODA H, IMANARI T. High-Resolution Proton Nuclear Magnetic Resonance Studies on Chondroitin Surfates.[J]. Analytical Sciences, 1993, 9(1):53-58. and MUCCI A, SCHENETTI L, VOLPI N. 1H and 13C nuclear magnetic resonance identification and characterization of components of chondroitin sulfates of various origin[J]. Carbohydrate Polymers, 2000, 41(1):37-45), $^1H$ and $^{13}C$ spectrums of HSB were classified, as shown in Table 3. $^1H$, $^{13}C$, HSQC and HMBC were analyzed comprehensively, finally getting that the primary unit structural formula of HSB is α-ΔGlcUA-[1→3]-GalNAc-4S.

TABLE 3

| $^1H$ and $^{13}C$ signal classification of HSB | | | | | | | | |
|---|---|---|---|---|---|---|---|---|
| Fragment | 1 | 2 | 3 | 4 | C-5 | 6 | NAc-1 | NAc-2 |
| GlcA-H | 4.47 | 3.38 | 3.59 | 3.79 | 3.67 | | | |
| GlcA-C | 103.39 | 72.07 | 73.34 | 80.19 | 76.27 | 174.96 | | |
| GalNAc-H | 4.57 | 4.03 | 4.02 | 4.75 | 3.84 | 3.79 | | 2.04 |
| GalNAc-C | 100.65 | 51.25 | 75.35 | 76.23 | 74.23 | 60.73 | 174.38 | 22.47 |

Application Example 1

Determination on the Inhibition of HSB on the Growth of Human Umbilical Vein Endothelial Cells by MTT Process Human umbilical vein endothelial cells in the logarithmic growth period (ECV304 cell strains purchased from Tongpai (Shanghai) Biotech Co., Ltd) were inoculated in a 96-well cell culture plate, with 100 μL cell suspension ($1.0\times10^4$ cells) per well. After cultivation for 12 h, 10 μL HSB solution (the solvent was normal saline) of different concentrations was added, so that the final concentrations were 25, 50, 100, 200 and 400 mg/L respectively. The control group was added with the same volume of culture solution. 4 parallel holes were set for each concentration, mixed fully and cultured for 48 h. 20 μL of MTT at 5 mg/mL was added into each hole and cultivation was continued for 5 h. 100 μL triple-fluid (1% of SDS, 5% of isobutanol, and HCl at 0.012 mol/L, W/V/V) was added into each hole and left at 37° C. for 12 h, then A values were determined at the wavelength of 570 nm. The experiment was repeated for 3 times to calculate the cell growth inhibitory rate, wherein the cell growth inhibitory rate=(1−Average A value of the experimental group/Average A value of the control group)×100%. The test results were shown in Table 4 and FIG. 13.

TABLE 4

| The inhibitory rate of HSB on the angiogenesis of human umbilical veins. | | | | | | |
|---|---|---|---|---|---|---|
| HSB Concentration (mg/mL) | 0 | 25 | 50 | 100 | 200 | 400 |
| Inhibitory rate (%) | 0 | 5.8 | 17.7 | 60.8 | 78.9 | 90.3 |

Figure 13:
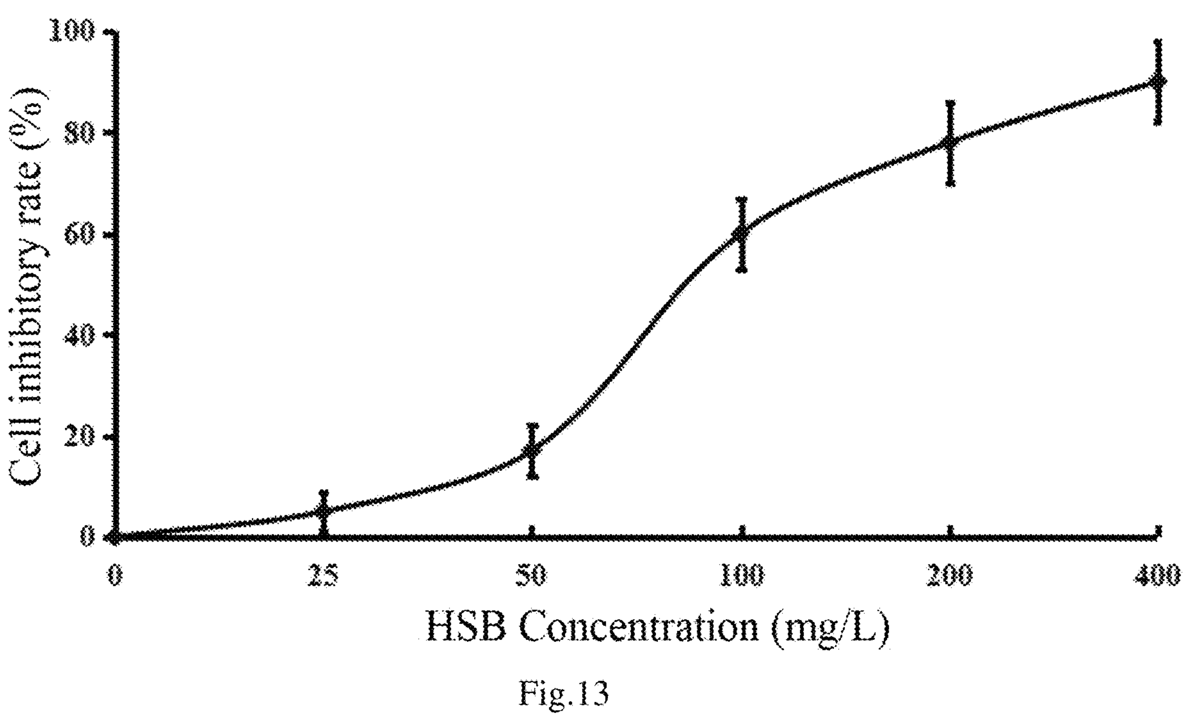
FIG. 13 is a diagram showing the inhibition effects of HSB on the growth of human umbilical vein endothelial cells.

It is known from Table 4 and FIG. 13 that, HSB can significantly inhibit the growth of human umbilical vein endothelial cells, and the inhibition effect is dose-dependent. The inhibitory rate of HSB at a concentration of 400 mg/L on the growth of human umbilical vein endothelial cells reaches up to 90.3%.

Application Example 2

Figure 14:
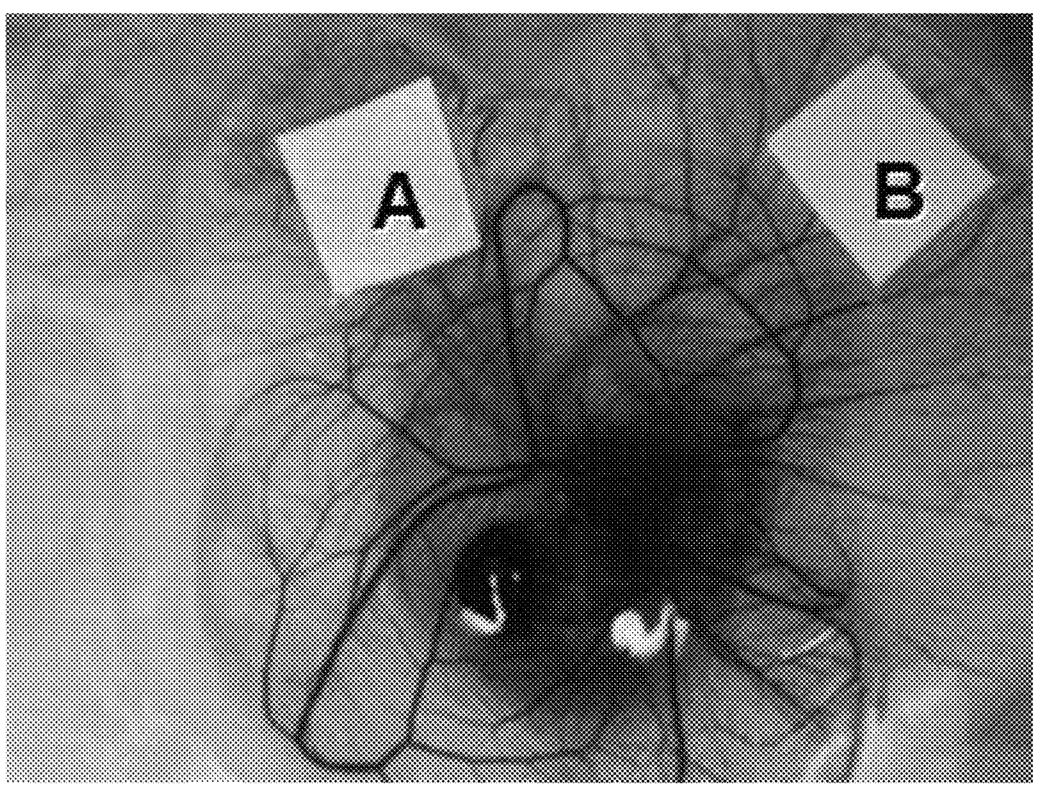
FIG. 14 is a physical image of chick embryo chorioallantoic membrane blood vessels, wherein, A indicates a region to be subsequently treated with HSB, and B indicates a region to be subsequently treated with PBS.
Figure 15:
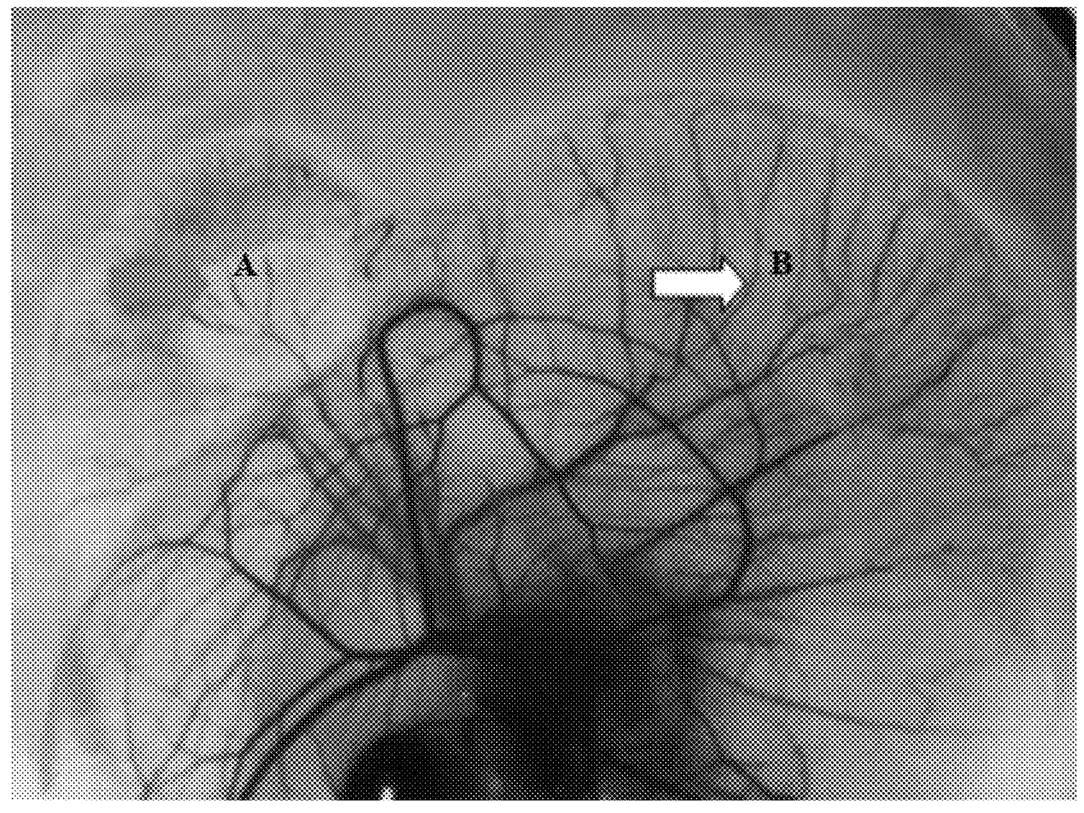
FIG. 15 is a physical image of chick embryo chorioallantoic membrane blood vessels after being treated with HSB and PBS respectively; wherein, A shows the status after being treated with HSB, and B shows the status after being treated with PBS.

Effect of HSB on CAM Angiogenesis:

Clean breeding eggs with homogeneous eggshell and uniform air chamber were selected, the stain was wiped away with 1‰ bromogeramine solution, and the eggs were sterilized with 75 v/v % alcohol. The eggs were divided into a control group and treatment groups of different sample concentrations, with 10 eggs per group. The eggs were incubated in an electric incubator at 37.8° C. for 1 week, placing a water tray in the incubator to keep the relative humidity at 40%~70%, and keeping an air hole to ensure the supply of oxygen. Under aseptic conditions, a small hole with a diameter of 1 cm was opened at the end of the embryo to form a pseudo-air chamber. Filter papers which had been immersed in 100 μL HSB solution (the solvent was normal saline) of different concentrations (0.25, 0.5 and 1 mg/mL) were placed on the chorioallantoic membrane in the air chamber, while an equal amount of PBS was added for the control group, and sealed with transparent adhesive tapes. Then, the eggs were incubated in a constant temperature incubator at 38° C., and then 100 μL HSB solution was added onto the filter papers 24 and 48 h later respectively, totally dosing for 3 times. After 72 h, they were immobilized with acetone and absolute ethanol for 15 min respectively, and then the membranes containing filter papers were cut and placed on glass slides. The filter papers were discarded. 5 visual fields were randomly selected under the microscope, and the number of branching points of blood vessels that can be seen within the coverage of filter papers was calculated and expressed as ±s. The angiogenesis inhibitory rate (%)=(1−the number of branching points of blood vessels in the dosing group/the number of branching points of blood vessels in the control group)×100%, with the calculation results shown in Table 5. The physical image of chick embryo chorioallantoic membrane blood vessels that have not been treated with HSB is shown in FIG. 14, and the physical image of chick embryo chorioallantoic membrane blood vessels that have been treated with HSB is shown in FIG. 15, wherein A shows the status after being treated with HSB, and B shows the status after being treated with PBS.

TABLE 5

The inhibitory rate of HSB on the angiogenesis of chick embryo chorioallantoic membrane

| HSB Concentration (mg/mL) | Number of breeding eggs | Number of branching points of blood vessels | Inhibitory rate (%) |
|---|---|---|---|
| 0 | 4 | 86.2 | — |
| 0.25 | 4 | 53.5 | 37.94 |
| 0.5 | 4 | 39.8 | 53.83 |
| 1 | 4 | 19.7 | 77.15 |

It can be known from Table 5 and FIGS. 14~15 that, the small branches of blood vessels and the density of blood vessels in the region that had been treated with HSB decreased significantly, suggesting that HSB can significantly inhibit the angiogenesis of chick embryo chorioallantoic membrane.

The description of the above examples is only intended to assist in understanding the method and core concept of the present disclosure. It should be noted that several improvements and modifications can be made to the present disclosure by persons with ordinary skills in the art without deviating from the principle of the present disclosure, all of which also fall within the protection scope of claims of the present disclosure. Various modifications to these examples are apparent to technical personnel in the art. General principles defined herein can be realized in other examples without deviating from the spirit or scope of the present disclosure. Therefore, the present disclosure shall not be confined to these examples set forth herein, but shall conform to the widest scope consistent with the principle and novel features disclosed herein.

What is claimed is:

1. A fish swim bladder-derived heparin-like mucopolysaccharide in an effective concentration for inhibiting angiogenesis, in blood vessels, wherein, the structural unit of the fish swim bladder-derived heparin-like mucopolysaccharide is α-ΔGlcUA-[1→3]-GalNAc-4S, and the fish swim bladder-derived heparin-like mucopolysaccharide comprises heparinoid accounting for 85.79±0.63% and protein accounting for 0.19±0.07%;

wherein, blood vessels comprise human umbilical veins, the effective inhibitory concentration of the fish swim bladder-derived heparin-like mucopolysaccharide on the human umbilical veins is 100~500 mg/mL, and an inhibitory rate of the fish swim bladder-derived heparin-like mucopolysaccharide at a concentration of 400 mg/L on the growth of human umbilical veins is 90.3%.

2. The fish swim bladder-derived heparin-like mucopolysaccharide of claim 1, wherein, the fish swim bladder-derived heparin-like mucopolysaccharide is prepared by a process comprising:

mixing fish swim bladder dry powder with water to obtain a suspension of fish swim bladder powder;

mixing and enzymatic hydrolyzing the suspension of fish swim bladder powder with sodium chloride and a protease to obtain enzymatic hydrolyzate;

inactivating the enzymatic hydrolyzate and then collecting a supernatant by centrifugation;

adsorbing the hydrolyzed heparin-like mucopolysaccharide the in the supernatant by macroporous anion-exchange resin and eluting the hydrolyzed heparin-like mucopolysaccharide the in the supernatant by an aqueous solution of sodium chloride to obtain an eluate;

precipitating and drying the eluate to obtain the fish swim bladder-derived heparin-like mucopolysaccharide;

wherein, the mass of sodium chloride is 1.2~1.8% of the mass of the fish swim bladder dry powder;

the mass of the protease is 0.5~3.0% of the mass of the fish swim bladder dry powder;

the concentration of the aqueous solution of sodium chloride to obtain the eluate is 0.3~1.1 mol/L;

the particle size of the fish swim bladder dry powder is 150~300 μm;

the mass ratio of the fish swim bladder dry powder to water for obtaining the suspension is 1:(25~30).

3. The fish swim bladder-derived heparin-like mucopolysaccharide of claim 2, wherein, the effective inhibitory concentration of the fish swim bladder-derived heparin-like mucopolysaccharide on the human umbilical veins is 300~400 mg/mL.

4. A composition comprising an effective concentration of a fish swim bladder-derived heparin-like mucopolysaccharide in preparation of angiogenesis inhibitors for human umbilical veins, wherein the structural unit of the fish swim bladder-derived heparin-like mucopolysaccharide is α-ΔGlcUA-[1→3]-GalNAc-4S, and the fish swim bladder-derived heparin-like mucopolysaccharide comprises heparinoid accounting for 85.79±0.63% and protein accounting for 0.19±0.07%;

wherein, the effective inhibitory concentration of the fish swim bladder-derived heparin-like mucopolysaccharide on the human umbilical veins is 100~500 mg/mL, and an inhibitory rate of the fish swim bladder-derived heparin-like mucopolysaccharide at a concentration of 400 mg/L on the growth of human umbilical veins is 90.3%.

5. The composition of claim 4, wherein, the effective inhibitory concentration of the fish swim bladder-derived heparin-like mucopolysaccharide on the human umbilical veins is 300~400 mg/mL.

6. A composition comprising an effective concentration of a fish swim bladder-derived heparin-like mucopolysaccharide in preparation of angiogenesis inhibitors for chick embryo chorioallantoic membrane blood vessels, wherein the structural unit of the fish swim bladder-derived heparin-like mucopolysaccharide is α-ΔGlcUA-[1→3]-GalNAc-4S, and the fish swim bladder-derived heparin-like mucopolysaccharide comprises heparinoid accounting for 85.79±0.63% and protein accounting for 0.19±0.07%;

wherein, the effective inhibitory concentration of the fish swim bladder-derived heparin-like mucopolysaccharide on the chick embryo chorioallantoic membrane blood vessels is 0.5~2 mg/mL, and an inhibitory rate of 1 mg/mL fish swim bladder-derived heparin-like mucopolysaccharide on the angiogenesis of chick embryo chorioallantoic membrane blood vessels is 77.15%.

7. The composition of claim 6, wherein, the effective inhibitory concentration of the fish swim bladder-derived heparin-like mucopolysaccharide on the chick embryo chorioallantoic membrane blood vessels is 1~1.5 mg/mL.

* * * * *